US006641523B2

(12) United States Patent
Ashenden

(10) Patent No.: US 6,641,523 B2
(45) Date of Patent: Nov. 4, 2003

(54) METHOD AND APPARATUS FOR REDUCING STRESS

(75) Inventor: Matthew Ashenden, London (GB)

(73) Assignee: Brainwave Limited, Jersey (GB)

( * ) Notice: Subject to any disclaimer, the term of this patent is extended or adjusted under 35 U.S.C. 154(b) by 44 days.

(21) Appl. No.: 09/999,882

(22) Filed: Oct. 31, 2001

(65) Prior Publication Data

US 2003/0023133 A1 Jan. 30, 2003

(30) Foreign Application Priority Data

Jul. 27, 2001 (GB) .............................................. 0118342

(51) Int. Cl.$^7$ ............................................. A61M 21/00

(52) U.S. Cl. ..................................................... 600/28

(58) Field of Search ............................ 600/26–28, 300; 128/897–898

(56) References Cited

U.S. PATENT DOCUMENTS 5,403,263 A * 4/1995 Rodgers ........................ 600/28
5,986,200 A * 11/1999 Curtin ........................... 84/609

FOREIGN PATENT DOCUMENTS

| DE | 42422568 A1 | 4/1994 | | |
| DE | 19647019 A1 | 5/1998 | | |
| DE | 1996158 A1 | 7/2001 | | |
| WO | 01/09874 A1 | * | 2/2001 | .................. 84/609 |

* cited by examiner

Primary Examiner—Samuel G. Gilbert
(74) Attorney, Agent, or Firm—Fulbright & Jaworski LLP

(57) ABSTRACT

A method and apparatus for relaxing and reducing stress in an individual is disclosed. The method involves exposing the individual to combined music, preferably anxiolitic music, and randomly selected voiceover. The apparatus comprises a system, suitable for performing the method, that is capable of reproducing a wide variety of different audio programs that comprises several phases, the content of each phase not being predictable in advance.

6 Claims, 5 Drawing Sheets

METHOD AND APPARATUS FOR REDUCING STRESS

Figure 1:
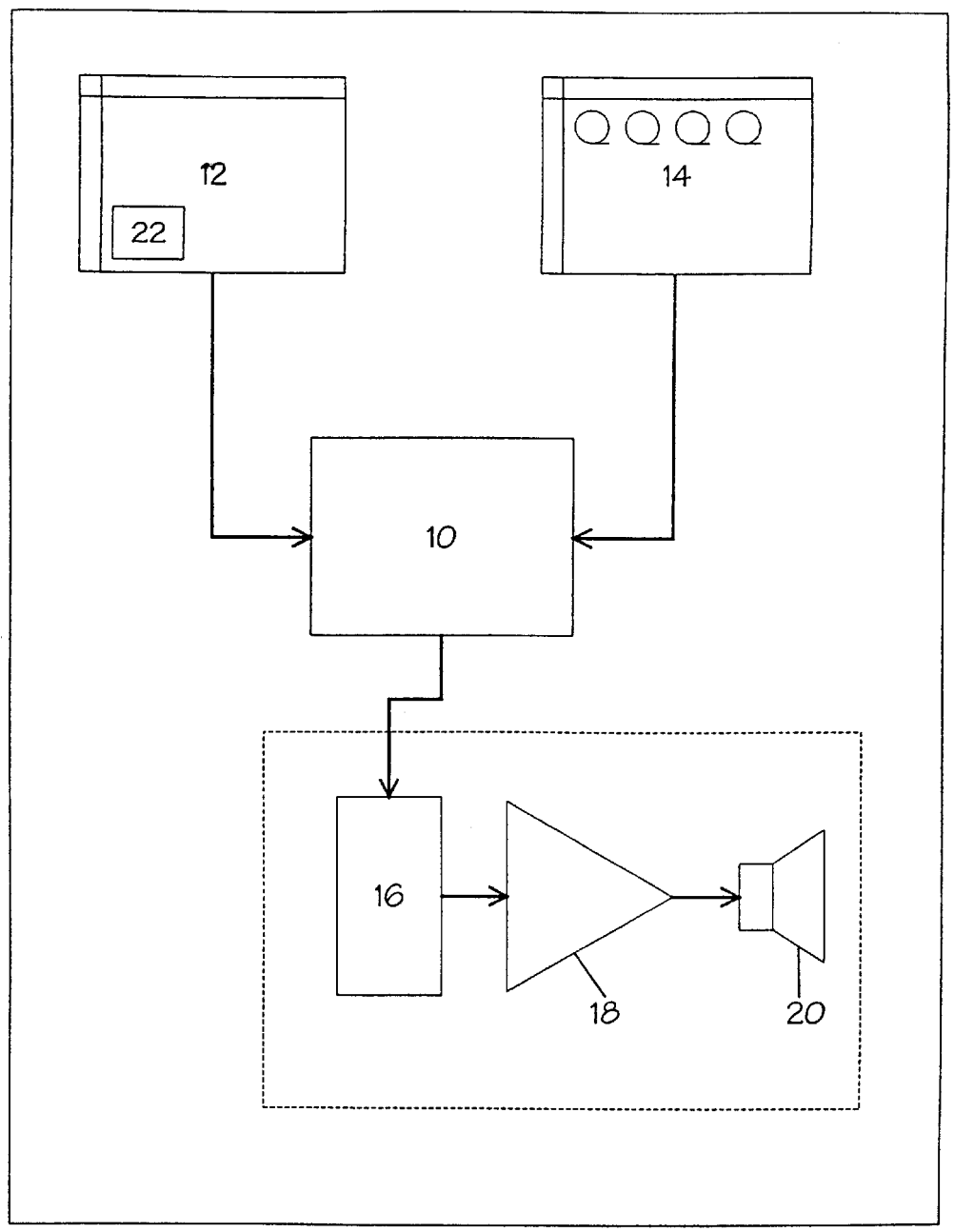
Figure 2:
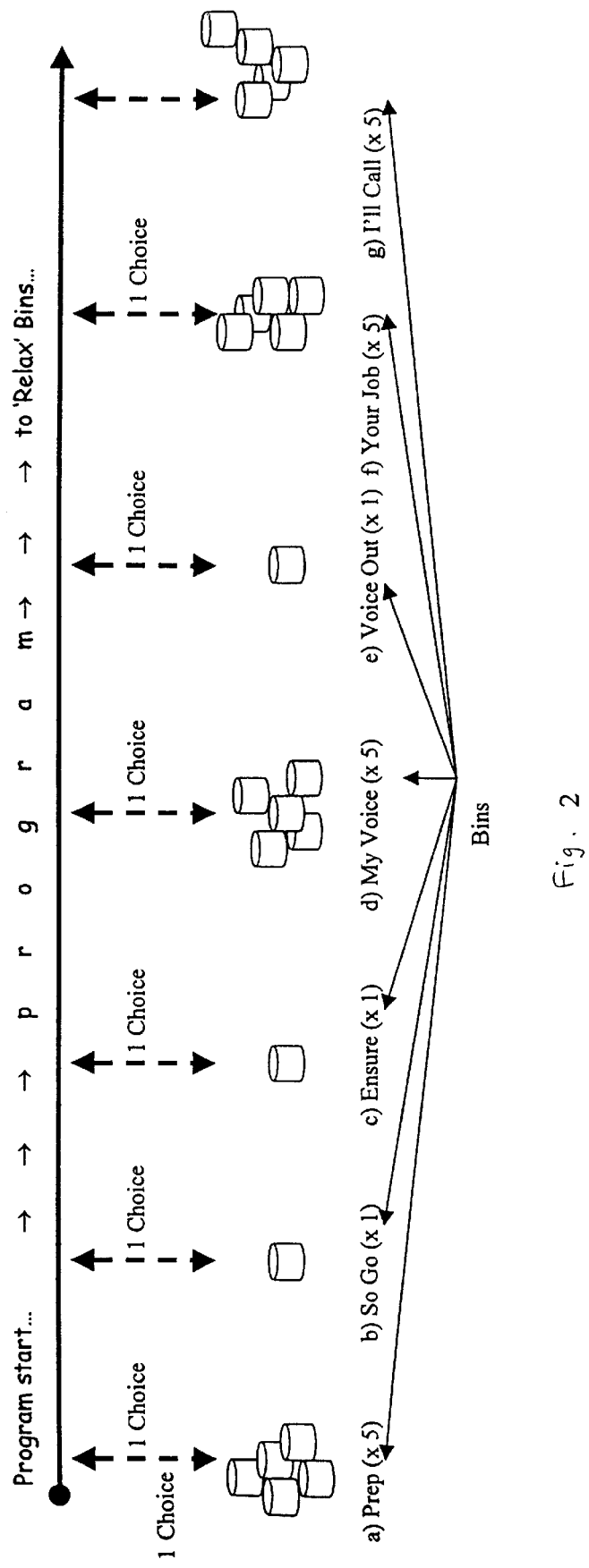
Figure 3:
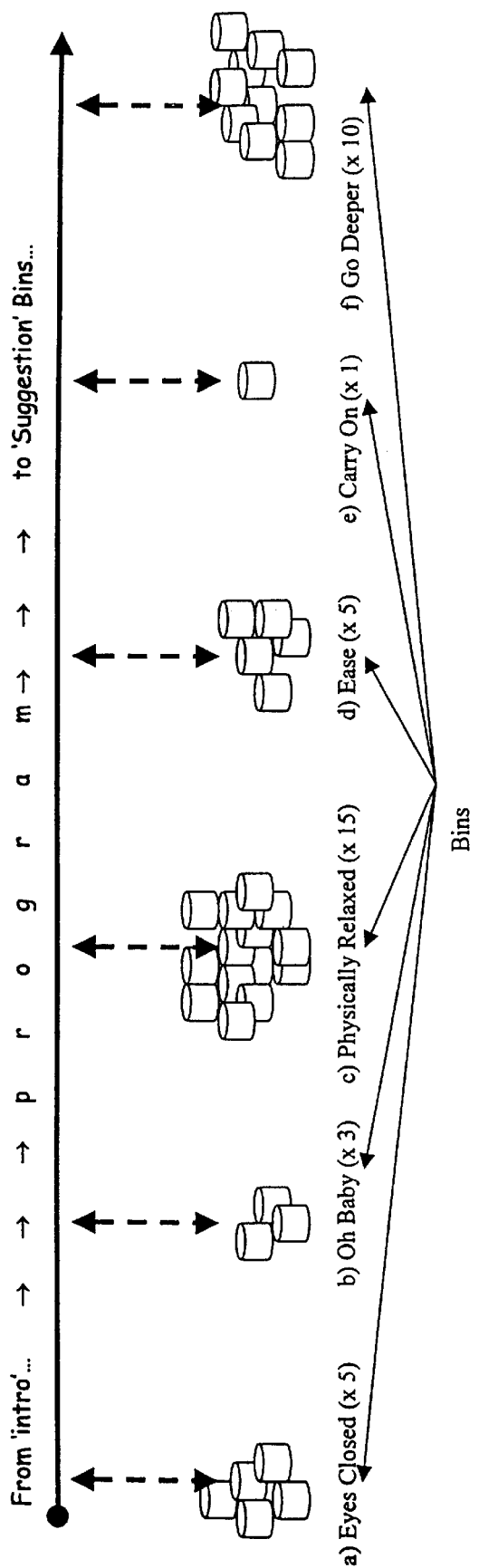
Figure 4:
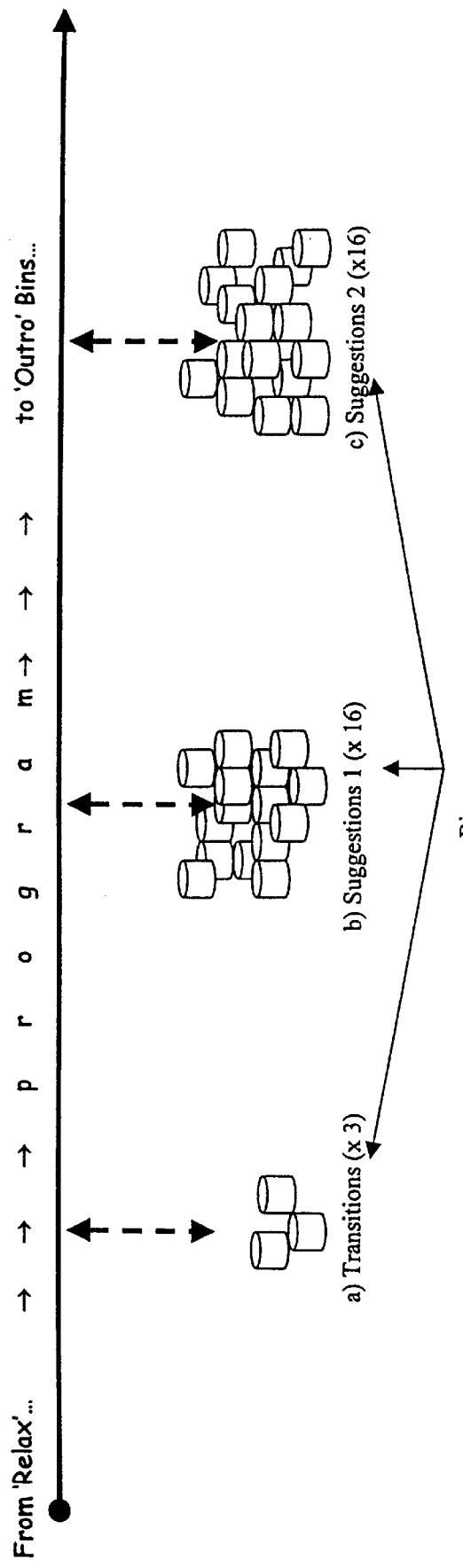
Figure 5:
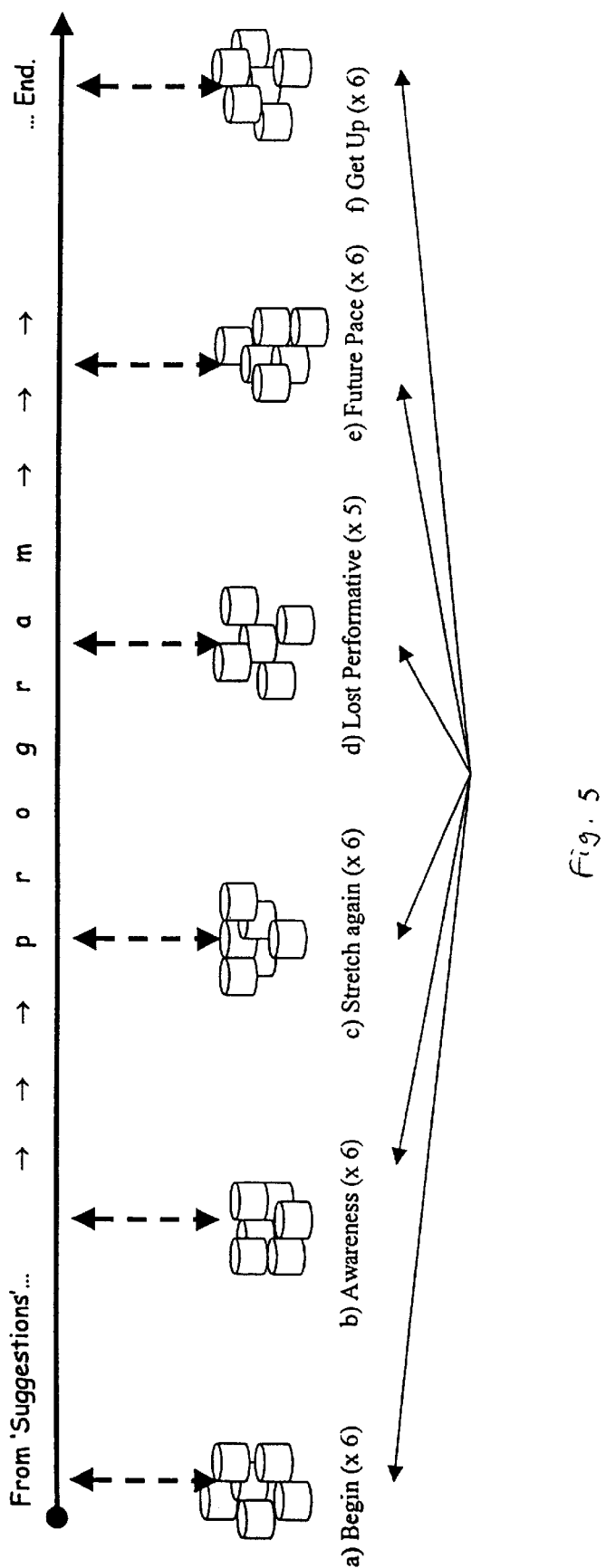

This invention concerns a method of relaxing and reducing stress in a patient and a device suitable for use therewith. More particularly, this invention concerns a method of relaxing and reducing stress in a patient through the use of music and voiceover.

U.S. Pat. No. 5,403,263 discloses a method of reducing anxiety and the recovery time of a patient during for the preoperative, intraoperative and postoperative phases of surgery. The method includes the steps of providing music in each phase of the surgery in combination with voiceover information relating to each phase of the surgery that the patient experiences at the time, with information, reassurance and suggestions to help the patient relax and feel comfortable during the three phases of surgery. The method relies upon utilization of an audio cassette tape player to play the music and voiceover to the patient. The recorder has a mechanical device that enables the tape player to reverse the tape automatically and play the other side in order to give the patient continuous music and voiceover instructions and suggestions for the length of each perioperative period. The voiceover information is particularly directed to the period of surgery which the patient is experiencing at the time. In addition to this information, repetitious voice suggestions are made to the patient to relax. The suggestions provide reassurance in order to reduce the tension, anxiety, stress and discomfort but most patients usually experience with surgery. The music of the system is anxiolytic, in that it is composed, without recognizable melody, familiar rhythm or harmony that can be anticipated, to reduce anxiety and to facilitate relaxation, and includes an opening theme, a middle section and closing theme, with the opening and closing themes being the same for each period the surgery.

The combination of anxiolytic music and voiceover has also been used successfully by individuals wishing to reduce anxiety and stress in their everyday lives. Typically, an individual will set aside a short period of time during their working day, for example 30 minutes during their lunch break, to listen to an audio cassette tape player playing a combination of anxiolytic music and voiceover. The music and voiceover are directed such that, as the individual listens to the tape, the individual may be caused to drift into a form of shallow sleep and then, as time progresses, the individual is slowly aroused, to awaken feeling relaxed and less stressed.

As an alternative to using an audio cassette tape player to listen to a pre-recorded cassette tape, the listener can use a CD or minidisk player to listen to an appropriately pre-recorded CD or minidisk.

Users, however, have noted that the relaxing and stress reducing effect they believe they derive from practicing this method tends to reduce as they expose themselves to repeated performances of the audiocassette tape. Further, they feel they do not receive the full benefit of a performance when, knowing that they do not have time to receive a full performance, they have to interrupt the performance and wake themselves up to go back to work rather than being woken up slowly by the tape. Various solutions which address these problems individually have been employed, such as using different tapes with different music and voiceover content and tapes with different performance lengths, but none of the prior art appears to address these problems together.

It is an object of the present invention, therefore, to provide an improved method of relaxing and for reducing stress in an individual. In another aspect, it is the object of the present invention to provide a method of relaxing and for reducing stress in an individual which does not suffer the problems of the prior art method, which employs pre-recorded cassette tapes, CDs or minidisks.

It should be understood that an inherently deterministic machine, such as a computer, cannot of itself, produce an output that is truly random. In the context of this specification, "random" and related phrases such as "randomly selected" should be understood as including (but is not limited to) "pseudo-random". The concept of functions that provide a pseudo-random output is well known to those knowledgeable in the field of computer programming, and are discussed in detail in Knuth, D. E.: The Art of Computer Programming, volume 2: Seminumerical Algorithms. Addison-Wesley, Reading, Mass., 3rd edition, 1997.

In accordance with a first aspect of the present invention, there is provided a method of relaxing and for reducing stress in an individual, which method comprises exposing said individual to a performance of music, preferably anxiolytic music, and randomly selected voiceover, and wherein the length of the overall performance is pre-determined by the individual. Preferably, the performance of music and randomly selected voiceover comprises at least the following sequential phases:

a) a first phase of combined music, preferably anxiolytic music, and voiceover, preferably randomly selected voiceover comprising instructions to lower said individual from a conscious state into a subconscious state;

b) a second phase of combined music, preferably anxiolytic music, and randomly selected voiceover comprising suggestions to maintain the individual in said subconscious state; and c) a third phase of combined music, preferably anxiolytic music, and voiceover, preferably randomly selected voiceover, comprising instructions to lift the individual from said subconscious state to a conscious state;

and wherein the length of the overall performance is pre-determined by the individual. Preferably, the music is randomly selected music, more preferably randomly selected anxioltic music.

Individuals using the method of the present invention on several occasions over a period of time may experience a feeling of improved relaxation and reduced stress, in comparison to the prior art method. Whilst it is not the intention of the inventors to be restricted by this theory, the inventors believe that the advantages of the present invention are achieved by:

a) the apparent randomness of the combined music and voiceover in each phase providing the individual with an unique performance on each exposure so that, in effect, the individual never becomes familiar with or is unable to predict at least a substantial part of the music and voiceover; and b) the ability of the individual to pre-select the length of time of the performance to fit in with the length of time the individual can actually spend on a performance between then normal activities (thereby eliminating the stress which the individual may otherwise experience if they know they have to interrupt the performance to resume normal activities).

Preferably, prior to the first phase a), the individual is exposed to an introduction phase of combined music, preferably anxiolytic music, and voiceover, preferably randomly selected voiceover, including a description of the nature of the method to follow.

The overall performance time is preferably from 10 to 60 minutes. Performance times longer than 60 minutes may be selected, but it is not recommended to select a performance time longer than 90 minutes.

The first phase a) and the third phase c) are preferably of the same or similar length in time, for example from 3 to 10 minutes each, whereas the second phase b) is preferably from 4 to 50 minutes.

As well as the voiceover being randomly selected, it is preferred that the anxiolytic music comprises randomly selected pieces of anxiolytic music.

In order to implement the first aspect of the invention, a system must be provided that is capable of reproducing a wide variety of different audio programmes that comprises several phases, the content of each phase not being predictable in advance. In practice, such a system will most typically include hardware that can execute a suitable software program. In principle it would be possible to make a large number of recordings for each of the phases, store them, and for the system select one of them at random for reproduction. However, to implement a system that can generate a reasonably large number of alternative audio programmes for each phase would require use of hardware having an unpractically large memory capacity.

From a second aspect, this invention provides a method for generating an audio programme, optionally in pursuance of a method embodying the first aspect of the invention, the programme having a plurality of phases, in which each phase is generated by selecting a plurality of audio sequences selected at random from a repertoire of audio sequences, and reproducing the selected audio sequences in succession. An entire phase is made up from several audio samples selected at random, so the audio programme that the phase represents has random content. A very large number of possible combinations, each representing a different audio program, can arise from such random selection, without the need to store multiple large audio programme files.

Each phase may comprise several phrases. Each phrase may comprise a predetermined number of audio sequences selected at random from a repertoire of one or more sequences specific to that phrase. For example, that repertoire of files may be associated with a so-called "bin" that is specific to a particular phrase of a phase of the programme. Where the bin for a particular phrase includes just one sequence, that sequence will be chosen each time an audio programme is generated with a probability of 1.

In some embodiments of the invention, it may be advantageous to ensure that one of more of the phases always lasts a predetermined length of time. Such phases are most typically formed from a predetermined and invariable number of sequences. This can be achieved by padding the phase with intervals of silence or an unobtrusive noise between successive audio sequences.

Moreover, some phases may have a variable length, for example, in order to ensure that the overall length of the programme in as near as possible to a target length (which may be variable). The sequences that can be selected to construct such phases may themselves be of different lengths, and the number of sequences used may be variable. In such embodiments, the selection of audio segments may be determined at least partially randomly and at least partly in accordance with a timing algorithm, with the aim being to produce a phase of a desired length.

Advantageously, no single audio sequence is selected more than once for inclusion in a single programme. Moreover, where the number of available audio sequences is sufficiently large, having once been selected, an audio sequence may be excluded from the repertoire available for selection until a predetermined number of programmes have been generated.

Each audio sequence is typically constituted by a digitally encoded audio signal. For example, each may be an audio media file, encoded in a recognised format, for instance that identified as MPEG layer 3 (MP3).

A method according to this aspect of the invention may be performed by hardware that has been designed specifically for reproduction of audio signals. Alternatively, it may be performed by a general-purpose computer having suitable audio reproduction hardware.

From a third aspect, this invention provides computer hardware having a program memory, a processor for executing a program stored in the program memory, a sequence memory in which is stored a plurality of audio sequences, and audio reproduction hardware, there being stored in the program memory a program which, when executed by the processor, causes the audio reproduction hardware to reproduce audio sequences stored in the sequence memory by a method according to the last-preceding aspect of the invention.

Computer hardware embodying this aspect of the invention may be designed specifically for reproduction of audio signals. It may, for example, be a portable or hand-holdable audio player. Alternatively, computer hardware embodying this aspect of the invention may be a general-purpose computer, such as a desktop personal computer, a notebook computer, a portable or handheld computer or a personal digital assistant.

The program memory (or some of the program memory) and/or the sequence memory (or some of the sequence memory) may be constituted within a non-volatile memory device, such as a ROM, EPROM, EEPROM, CMOS, Flash or other suitable device known or yet to be developed (for convenience referred to generally within this specification as a "ROM"). The ROM may be provided in a configuration that can be readily exchanged by a user, such as in a cartridge or a card. There may additionally be program memory and/or sequence memory that is permanently or semi-permanently installed within the hardware.

From yet a further aspect, the invention provides a computer program product executable by computer hardware to perform a method according to the last-but-one preceding aspect of the invention. Typically, such a computer program product is executable by hardware embodying the last preceding aspect of the invention.

A computer program product embodying this aspect of the invention may be provided stored in a memory device such as a ROM or a machine-readable data carrier such as a disc (e.g. a magnetic or optical disc). A memory device containing a computer program product embodying this aspect of the invention may also contain data representing one or more audio sequences. In such cases, the computer program product may be executable by computer hardware to reproduce a plurality of such audio sequences to perform a method according to the last-but-one preceding aspect of the invention.

An embodiment of the invention shall now be further described by way of exemplification and with reference to the accompanying drawings, in which:

FIG. 1 is a block diagram of computing apparatus for use in an embodiment of the invention; and FIGS. 2 to 5 illustrate selection of audio segments respectively in introduction, first, second and third phases of an audio programme generated in pursuance of the invention.

With reference first to FIG. 1, computing apparatus for use in this invention is embodied as a compact, self-contained portable player.

The player comprises a microprocessor 10 that is connected to a program memory 12 and a sequence memory 14. In addition, the player includes an audio output stage that includes a digital-to-analogue converter (DAC) 16, and amplifier 18, and a transducer 20. The transducer may, for example, by a loudspeaker or a component part of a headphone.

The program memory 12 contains a software program that can be executed by the microprocessor. The program memory may include a kernel 22 that contains a basic operating system for the computing device and an application program that provides the desired functionality for the device. While the kernel will typically be stored on a ROM device permanently installed in the player, the application program and the sequence memory 14 is contained within a memory device that can readily be removed from the player by a user; for example, in the form of a memory card. In this way, the detailed function and programme repertoire of the player can be changed by a user by changing one memory card for another.

The sequence memory 14 contains a multiplicity of data files, each being an audio signal encoded (in this embodiment) in MP3 format. The purpose and content of these sequences will be described in detail below.

The microprocessor 10 executes the program stored in the program memory 12. Under control of that program, the microprocessor can retrieve a file from the sequence memory 14, decode the file, and instruct the DAC 16 to convert the decoded file to an analogue audio signal. The analogue audio signal is then reproduced by the transducer 20 as sound audible to a user.

The application program operates to create an audio programme by sequential reproduction of many of the audio files. The entire programme is, on a detailed level, apparently random, but has a closely defined large-scale structure. Specifically, the programme has four phases: an introduction phase, a first phase, a second phase and a third phase. Each phase is formed from a plurality of series, each series including one or more audio files.

Each of the audio files in the sequence memory is associated with one or more file group referred to as a "bin". Each bin is associated with one of the phrases. In order to generate a phase, the application program selects at random a file from each of the bins associated with that phase in turn. In this typical embodiment, the random selection is based upon the output value of a pseudo-random function. Such a function can give an appearance of randomness that is sufficient for this application. While it will be recognise that hardware systems can be provided to give a truly random output, this is unlikely to be necessary for the purposes of embodying this invention. Note that some bins may contain just one file, in which case it is selected for reproduction in each programme. Once a file is selected, it is reproduced using the audio output stage of the player. In some cases, a phrase is included more than once in a phase. In this instance, multiple files are selected in turn from the one bin.

In order to enhance the programme output, the processor may maintain a table of selected files. In that case, once a file is selected in any programme, it will not be eligible for subsequent selection within that programme. Optionally, it may be excluded from selection from one or more further programmes.

In FIGS. 2 to 5, each figure represents one phase of a programme, and each bin is represented as one or more files associated with a choice. The audio programme is constructed as will now be described.

Introduction Phase

During the introduction phase, if present, the individual is exposed to a combination of anxiolytic music and randomly selected voiceover, including a description of the nature of the method to follow. In one particular embodiment of this phase, the individual is exposed to a sequential series of phrases which, when combined, collectively form a logical description of the nature of the method to follow. Each phrase within the series is randomly selected from a group comprising one or more phrases.

For example, the voiceover description of an introduction phase may comprise the sequential combination of phrases I.A, I.B, I.C, I.D, I.E, I.D, I.F, and I.G, each phrase being randomly selected from the groups of phrases listed below:

Series I.A
I.A.01 Before you settle yourself down into a deeply refreshing nap
I.A.02 Now that you have set aside this time to relax and nap
I.A.03 While you are settling down and making yourself comfortable
I.A.04 As you're preparing for a deeply refreshing rest
I.A.05 Now that you are getting ready to enjoy some rest and relaxation
I.A.06 To make the most of this time that you set-aside
I.A.07 In preparing to yourself to relax and recharge
I.A.08 Begin settling yourself down
I.A.09 While you are preparing to rest and deeply
I.A.10 Now that you have taken this time to rest and recharge Series I.B
I.B.01 Its a good idea to ensure that you will not be disturbed and that you can be as comfortable as possible both physically and mentally. Find a position for your body where you can relax completely so that its easier for you to let go of all the events of the day so far, for a little while and get as much benefit as possible from this time out.

Series I.C
I.C.01 I will offer you some guidance for a few minutes to assist you in relaxing as completely as possible and then from time to time I'll offer quiet ideas and reminders in the background.
I.C.02 My voice will be here as an occasional guide to remind you to relax just that little bit more and to help you get as much benefit as you can from this time you have set aside.
I.C.03 For a few minutes I will guide you while you begin to relax, but then, just let my voice fade into the background.
I.C.04 I will offer you some advice for just a little while and then, while you just let yourself drift off, I will from time to time offer an idea or some advice that you can incorporate into your rest.
I.C.05 I will guide you for a little while and then while you rest quietly I'll offer some gentle ideas and reminders as you continue to rest.
I.C.06 I will continue offering occasional quiet guidance for a few minutes while you begin relaxing and allow your mind to become more calm.
I.C.07 And for a few minutes my voice will accompany you offering ideas or advice while you relax as deeply as possible.
I.C.08 As you begin relaxing, I will continue speaking from while offering some quiet hints and ideas.

Series I.D
I.D.01 At any time, you can make my voice fade into the background by gently relaxing your attention into what is most comfortable and pleasant inside.

Series I.E

I.E.01 For the time you have set aside your job is to relax with comfort and ease and allow yourself to drift off into a pleasant and refreshing nap.

I.E.02 All I want you to do is let your mind and body slide with ease and comfort into a pleasant and refreshing nap.

I.E.03 All you need to do is let your body and mind become more and more relaxed and go into an effortless and refreshing nap.

I.E.04 The only thing you need to pay attention to is comfort and ease. Let your mind and body relax into a quiet and refreshing nap.

I.E.05 There's no need for effort, no need for concentration—only let your mind and body relax and relax more into a deeply refreshing and pleasant nap.

I.E.06 For the time you have set aside, your job is to relax in comfort and ease and allow yourself to drift off into a pleasant and refreshing nap.

I.E.07 All I want you to do you select your mind and body slide with ease and comfort into a pleasant and refreshing nap.

I.E.08 All you need to do is let your body and mind become more and more relaxed and go into an effortless and refreshing nap.

I.E.09 The only thing you need to pay attention to his comfort and ease. Let your mind and body relax into a quiet and refreshing nap.

I.E.10 There's no need for effort, no need for concentration—only let your mind and body relax and relax more into a deeply refreshing and pleasant nap.

Series I.F

I.F.01 And when the time you have programmed for your rest is up, I will ask you to return refreshed, relaxed and alert.

I.F.02 When its time for you to wake up and return to your day, I will gently call and remind you that its time to return.

I.F.03 I'll be here to remind you when its time to wake up and return to your day refreshed, relaxed and alert.

I.F.04 At the proper time, I will let you know that its time to return and rejoin the day.

I.F.05 And when your napping time is complete, I will remind you to wake up and rejoin your day relaxed, refreshed and alert.

I.F.06 And when the time you have programmed for your rest is up, I will ask you to return refreshed, relaxed and alert.

I.F.07 When it's time for you to wake up in return to your day, I will gently call and remind you that it's time to return.

I.F.08 I'll be here to remind you when it's time to wake up and return you to your daily refreshed, relaxed and alert.

I.F.09 At the proper time, will I will let you know that it's time to return and rejoined the day.

I.F.10 And when you're napping time is complete, I will remind you to wake up and rejoin your day relaxed, refreshed and alert.

Series I.G

I.G.01 So now you can just relax and let your mind and body slide into a deeply refreshing and pleasant nap.

I.G.02 So now you can just relax and let your mind embody slide into a deeply refreshing and pleasant nap.

First Phase

During the first phase the individual is exposed to a combination of anxiolytic music and randomly selected voiceover comprising instructions to lower said individual from a conscious state to a subconscious state. In one particular embodiment of this phase, the individual is exposed to a sequential series of phrases which, when combined, collectively form a logical set of instructions to follow. Each phrase within the series is randomly selected from a group comprising one or more phrases.

For example, the voiceover instructions of a first phase may comprise the sequential combination of phrases II.A, II.B, II.C, II.D, II.E, II.D and II.F, each phrase being randomly selected from the groups of phrases listed below:

Series II.A

II.A.01 Close your eyes, if you haven't already and take a moment to stretch your body—your neck, arms, hands, back, legs and feet.

II.A.02 Close your eyes, stop a moment and first tense all the muscles of your body, hold it, hold it, hold it and now allow your body to relax completely.

II.A.03 Close your eyes, if you haven't already and set aside any concerns or considerations for a little while. Just stop a moment and have a stretch of all your muscles and now relax.

II.A.04 Close your eyes, and yawn—a good deep yawn and stretch that starts at the top of your head and goes all the way down to the tip of your toes.

II.A.05 With your eyes closed, I want you to tense the muscles of your body—each and every part of your body and hold it for a moment and now relax.

Series II.B

II.B.01 and really enjoy the feeling.

II.B.02 and allow yourself to luxuriate in that feeling.

II.B.03 and really notice how good it feels

Series II.C

II.C.01 allow your breathing to soften, with each breath you take. Just quietly and gently say to yourself, soften and relax II.C.02 let each muscle from the top of your head to the bottom of your toes continue to relax, each part II.C.03 what would it be like if you're twice as relaxed as you are right now? Imagine just how good it would feel II.C.04 notice where you feel most relaxed in your body and imagine that feeling spreads.

II.C.05 simply let your attention go and allow your body to become that much more quiet and relaxed II.C.06 let each muscle in your body and part of your mind become quieter, more comfortable and more relaxed II.C.07 make each out breath easier than the one before, and each in breath more relaxed.

II.C.08 with each breath you take allow yourself to be even more relaxed than you were before II.C.09 at any time if you want to you can just let yourself gently fall asleep, its okay II.C.10 place gentle awareness on increasing comfort anywhere you begin to notice it II.C.011 with each breath allow each muscle in your body to relax that much more II.C.012 even your muscles like to quiet down and rest when you give them the opportunity II.C.013 each breath can be another step deeper into pleasant and relaxing feelings II.C.014 when you're relaxing let even the little muscles in your face—your mouth, eyes and forehead and even your head muscles relax II.C.015 your fingers and toes can relax as much as any other part of your body Series II.D II.D.01 let all of this happen easily, without effort, simply relax and permit it to happen II.D.02 relaxation is not an effort just gently allow it to happen II.D.03 simply allow yourself the deep pleasure in relaxation
II.D.04 permit yourself to float deeper into these enjoyable sensations
II.D.05 just let it happen, easily and gently
Series II.E
II.E.01 while you are relaxing let whatever thoughts float through your mind carry on their way
II.E.02 while you are relaxing let your thoughts drift. There may be thoughts but you are not obliged to think them
II.E.03 And you can let your mind relax as much, if not more than your body
II.E.04 if you want you can let your mind go and find some pleasant and enjoyable memory
II.E.05 and you may find yourself drifting in daydreams and pleasant thoughts—that's alright just let them come and go
II.E.06 thoughts can come and go—just let them pass through like clouds in the sky
II.E.07 let thoughts be like soft daydreams, quiet and slow. It's alright to be quiet for little while
II.E.08 if you think—think softly and quietly—there's no need now for more than a whisper
II.E.09 let your mind be absorbed in calm and rest
II.E.010 when your beginning to feel very relaxed—let your mind feel that relaxed as well
Series II.F
II.F.01 carry on, just as you are until you are happy simply drifting more deeply into relaxing and pleasant thoughts Second Phase During the second phase the individual is exposed to a combination of anxiolytic music and randomly selected voiceover comprising suggestions to maintain the individual in said subconscious state. In one particular embodiment of this phase, the individual is exposed to a sequential series of phrases which, when combined, collectively form a logical set of suggestions. Each phrase within the series is randomly selected from a group comprising one or more phrases.

For example, the voiceover instructions of a second phase may comprise the sequential combination of phrases III.A, III.B, III.C and III.D, each phrase being randomly selected from the groups of phrases listed below:

Series III.A
III.A.01 while you are resting
III.A.02 and while you continue, just as you are
III.A.03 as you go on enjoying your relaxation
Series III.B
III.B.01 somewhere at the back of your back of your mind you might begin to consider that
Series III.C
III.C.01 a small rest can produce big benefits
III.C.02 when you really relax deeply, it can seem like time is suspended or even stretched out
III.C.03 you can feel good for looking after yourself
III.C.04 relaxing more deeply is a skill that can improve your health
III.C.05 even a short rest can help you feel deeply refreshed
III.C.06 a little quiet time during the day can help you sleep better at night
III.C.07 when you are more relaxed and release stress in a calm and safe way, you can be more relaxed others
III.C.08 the more deeply you relax, the more energised you will feel
III.C.09 learning to relax quickly and deeply is a powerful skill that can help all areas of your life
II.C.010 even resting quietly with your eyes closed for a short time can be profoundly beneficial to you
II.C.011 just letting yourself drift once in awhile gives your body and mind an opportunity to recuperate
III.C.012 when you are resting comfortably, your mind has a chance to slow down and reset itself
III.C.013 you're learning to relax is a skill that will really help you when the pressure is on
III.C.014 as you become more skilled in taking time outs— you will feel more and more refreshed
III.C.015 the more you relax now, the better you feel
III.C.016 when you notice pleasant feelings inside— imagine them spreading all over your body
Series III.D
III.D.01 sometimes little day dreams can be of help to you
III.D.02 working hard and relaxation go together
III.D.03 your body knows how to safely and quickly release stress and process your problems while you rest quietly
III.D.04 thoughts are just thoughts and not reality
III.D.05 sometimes using a little less effort but more careful planning can make all the difference in your life
III.D.06 rest and recovery go together
III.D.07 what will it be like when you achieve the things that you want to, more easily than you expected?
III.D.08 its amazing how good you can feel when you've taken the time to refresh yourself
III.D.09 even deep stress and problems can be safely resolved at the appropriate speed, with ease and comfort
III.D.010 you can be delightfully surprised at how good you feel after you awaken
III.D.011 remember to bring your relaxation into the areas of your life where its needed
III.D.012 allow yourself to really enjoy the things you do
III.D.013 later on remember to relax as you go about your day
III.D.014 relaxation and feeling good are habits like any other—the more you practice, the better you become
III.D.015 while your resting, its a good time for solutions and ideas to form in the back of your mind
III.D.016 just relaxing comfortably can help the good ideas in the back of your mind to find an appropriate form Third Phase During the third phase the individual is exposed to a combination of anxiolytic music and randomly selected voiceover comprising instructions to lift the individual from said subconscious state to a conscious state. In one particular embodiment of this phase, the individual is exposed to a sequential series of phrases which, when combined, collectively form a logical set of instructions to follow. Each phrase within the series is randomly selected from a group comprising one or more phrases.

For example, the voiceover instructions of a first phase may comprise the sequential combination of phrases IV.A, IV.B, IV.C, IV.D, IV.E, IV.D and IV.F, each phrase being randomly selected from the groups of phrases listed below:

Series IV.A
IV.A.01 In a few moments, I'm going to ask you to begin to bring your attention back to normal waking
IV.A.02 in a minute I will ask you to begin to wake up, but not just yet
IV.A.03 I'm going to ask you, in a moment to begin to return from your nap
IV.A.04 I am going to ask you in a moment or two to begin to wake yourself up
IV.A.05 In a moment I will ask you to begin to wake yourself up but not just yet
IV.A.06 I will ask you in a moment or two to begin to 'rouse yourself from your nap Series IV.B IV.B.01 bring your attention back slowly and gently to the sensations in your body IV.B.02 let your awareness come back to the sensations in your body IV.B.03 gently allow your mind to begin noticing the pleasant sensations in your body IV.B.04 bring your awareness to the pleasant sensations in your body IV.B.05 notice the sensations in your body. where do you feel most comfortable?

IV.B.06 let you're attention move to the feelings in your body

Series IV.C

IV.C.01 Before you fully awaken take a moment and gently stretch once again

IV.C.02 Now slowly and gently begin to stretch your body and really enjoy the sensations IV.C.03 Take a moment and give yourself another good stretch IV.C.04 Now take a moment and deeply stretch again—from top to toe IV.C.05 And now take a moment to really stretch and even a good yawn too IV.C.06 Now, I want you to give yourself a really good stretch—one that stretches your whole body Series IV.D IV.D.01 taking a timeout can be a deeply refreshing and beneficial experience IV.D.02 Its good that you have taken this time to recharge and refresh yourself IV.D.03 taking a little siesta now and then can IV.D.04 taking a timeout and allowing your body and mind to reset themselves is a good thing.

IV.D.05 its a good thing to take time out now and then and refresh yourself

IV.D.06 you know, the benefits of this nap can stay with you for the rest day

Series IV.E

IV.E.01 take a moment now and think about what you want to do with benefits you've gained by taking this time out IV.E.02 now, think about how your going to use the benefits of this nap IV.E.03 just take one more moment and think through how you are going to use your energies for the rest of the day IV.E.04 now why not think about how you are going to be using your energies for the rest of the day IV.E.05 now think for moment how you want to use your energies for the rest of the day IV.E.06 take a moment now to think through the rest of your day Series IV.F IV.F.01 Alright, its time for you wake up and rejoin the day!

IV.F.02 Okay, you've had a rest now and its time for you to fully wake up and return to your day IV.F.03 Alright, its time to fully wake yourself up now—come on back and rejoin the day.

IV.F.04 Alright, now its time to 'rouse yourself and rejoin your day

IV.F.05 Okay, now rouse yourself—its time to get going and rejoin the world

IV.F.06 Alright, now wake yourself up. Its time to come back and rejoin the day.

During each of the above phases, the individual is exposed to anxiolytic music, which music is composed to reduce anxiety and to facilitate relaxation, having no recognizable melody, familiar rhythm or harmony that can be anticipated.

The method of the present invention may be used in the manner described in the U.S. Pat. No. 5,403,263 or it may be used by individuals wishing to relax and reduce their stress levels during the working day.

What is claimed is:

1. A method of relaxing and for reducing stress in an individual, which method comprises exposing said individual to a performance of music and randomly selected voiceover, and wherein the length of the overall performance is pre-determined by the individual.

2. A method of relaxing and for reducing stress in an individual as claimed in claim 1, which method comprises exposing said individual to a performance of music and voiceover comprising at least the following sequential phases:

a) a first phase of combined music and randomly selected voiceover comprising instructions to lower said individual from a conscious state into a subconscious state;

b) a second phase of combined music and randomly selected voiceover comprising suggestions to maintain the individual in said subconscious state; and c) a third phase of combined music and randomly selected voiceover comprising instructions to lift the individual from said subconscious state to a conscious state;

d) and wherein the length of the overall performance is pre-determined by the individual.

3. A method as claimed in claim 2, wherein prior to the first phase a) the individual is exposed to an introduction phase of combined music and randomly selected voiceover including a description of the nature of the method to follow.

4. A method as claimed in any one of claim 2, wherein the overall performance time is from 10 to 60 minutes.

5. A method as claimed in claim 2, wherein the first phase a) and the third phase c) are of the same or similar length in time.

6. A method as claimed in claim 1, wherein the music is anxiolytic music and comprises randomly selected pieces of anxiolytic music.

* * * * *